United States Patent
Ohyu et al.

(10) Patent No.: US 8,520,915 B2
(45) Date of Patent: Aug. 27, 2013

(54) MEDICAL IMAGE DIAGNOSIS APPARATUS SPECIFYING A SPOT ON A PROJECTION IMAGE FOR SUBSEQUENT 3D IMAGING

(75) Inventors: Shigeharu Ohyu, Yaita (JP); Hitoshi Yamagata, Otawara (JP); Keisuke Hashimoto, Nasushiobara (JP); Atsuko Sugiyama, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1325 days.

(21) Appl. No.: 11/854,107

(22) Filed: Sep. 12, 2007

(65) Prior Publication Data
US 2008/0063136 A1    Mar. 13, 2008

(30) Foreign Application Priority Data
Sep. 13, 2006    (JP) ................. 2006-248401

(51) Int. Cl.
*G06K 9/00*    (2006.01)
(52) U.S. Cl.
USPC ........................................................ 382/128
(58) Field of Classification Search
USPC ........................................ 382/128; 345/420
See application file for complete search history.

(56) References Cited

U.S. PATENT DOCUMENTS

| | | | | |
|---|---|---|---|---|
| 6,011,862 A * | 1/2000 | Doi et al. | ...... | 382/132 |
| 6,084,592 A * | 7/2000 | Shum et al. | ...... | 345/420 |
| 6,549,803 B1 * | 4/2003 | Raghavan et al. | ...... | 600/431 |
| 2003/0215120 A1 * | 11/2003 | Uppaluri et al. | ...... | 382/128 |
| 2004/0068167 A1 | 4/2004 | Hsieh et al. | | |
| 2004/0252870 A1 * | 12/2004 | Reeves et al. | ...... | 382/128 |
| 2005/0105683 A1 * | 5/2005 | Sato | ...... | 378/62 |
| 2005/0254617 A1 * | 11/2005 | Nishide et al. | ...... | 378/4 |
| 2006/0058605 A1 * | 3/2006 | Deischinger et al. | ...... | 600/407 |

FOREIGN PATENT DOCUMENTS

| | | |
|---|---|---|
| JP | 4-5953 | 1/1992 |
| JP | 7-23946 | 1/1995 |
| JP | 8-166995 | 6/1996 |
| JP | 2001-513923 | 9/2001 |
| JP | 2002-360562 | 12/2002 |
| JP | 2003-91735 | 3/2003 |
| JP | 2003-116842 | 4/2003 |
| JP | 2003-275199 | 9/2003 |
| JP | 2004-105731 | 4/2004 |
| JP | 2004-174261 | 6/2004 |
| JP | 2005-34473 | 2/2005 |

(Continued)

OTHER PUBLICATIONS

U.S. Appl. No. 11/736,865, filed Apr. 18, 2007, Sumiaki Matsumoto, et al.

(Continued)

*Primary Examiner* — Hadi Akhavannik
(74) *Attorney, Agent, or Firm* — Oblon, Spivak, McClelland, Maier & Neustadt, L.L.P.

(57) ABSTRACT

A medical image diagnosis apparatus designates an imaging range of a subject from a projection image for designation of the imaging range, specifies a specific spot on the projection image, performs scanning for generating a three-dimensional medical image of the subject on the basis of the imaging range, finds out a three-dimensional target region from the three-dimensional medical image on the basis of the specific spot, and detects a candidate for an abnormal part in the three-dimensional target region.

13 Claims, 6 Drawing Sheets

(56) References Cited

FOREIGN PATENT DOCUMENTS

| | | |
|---|---|---|
| JP | 2005-143622 | 6/2005 |
| JP | 2006-55635 | 3/2006 |
| JP | 2006-68229 | 3/2006 |
| JP | 2006-102508 | 4/2006 |
| JP | 2006-2390105 | 9/2006 |
| JP | 2007-44508 | 2/2007 |
| WO | WO 2006/085254 A1 | 8/2006 |

OTHER PUBLICATIONS

Japanese Office Action mailed Jul. 19, 2011, in Japanese Patent Application No. 2006-248401 filed Sep. 13, 2006 (with English Translation).

Final Office Action issued Apr. 10, 2012 in Japanese Patent Application No. 2006-248401(with English translation).

\* cited by examiner

MEDICAL IMAGE DIAGNOSIS APPARATUS SPECIFYING A SPOT ON A PROJECTION IMAGE FOR SUBSEQUENT 3D IMAGING

CROSS-REFERENCE TO RELATED APPLICATIONS

This application is based upon and claims the benefit of priority from prior Japanese Patent Application No. 2006-248401, filed Sep. 13, 2006, the entire contents of which are incorporated herein by reference.

BACKGROUND OF THE INVENTION

1. Field of the Invention

The present invention relates to a medical image diagnosis apparatus for diagnosing a diseased part from a CT image or MRI image of a subject, an X-ray CT apparatus that acquires a CT image, and an image processor that detects a candidate for an abnormal part from the CT image or MRI image.

2. Description of the Related Art

A computer-aided diagnosis (hereinafter referred to as "CAD") apparatus receives a reconstructed image of a subject acquired by, for example, an X-ray CT apparatus. The CAD apparatus executes a diagnosis-assisting algorithm corresponding to a corresponding tissue region, such as a lung field region, from the reconstructed image of the subject received from, for example, the X-ray CT apparatus, thereby detecting a diseased part. As such, the CAD apparatus processes an image of a subject, such as a patient, which is acquired clinically, using a computer, then detects the feature or part of a disease of a target tissue region, for example, a lung cancer of a lung field region or a liver cancer of a liver region, and then digitalizes the features of the disease, thereby supporting doctor's diagnosis.

The image of the subject, such as a patient, is a reconstructed image (CT image) that is obtained by acquiring plural kinds of projection data of a subject by, for example, an X-ray CT apparatus, and reconstructing the projection data. The feature or part of the disease acquired by the CAD apparatus, or the digitalized data of the feature of the disease is transmitted to, for example, an image reading terminal.

In executing the CAD apparatus to support doctor's diagnosis, it is necessary to designate an extracted position of a target tissue region from a CT image acquired by the X-ray CT apparatus prior to execution of the CAD apparatus. This is because the image of the target tissue region in the subject is extracted from the CT image.

The designation of the extraction position of the target tissue region is performed by user's operation. For example, when the feature or part of a liver cancer is detected automatically and the feature of the liver cancer is digitalized, identification of a liver region is required before the diagnosis-assisting algorithm is executed in the CAD apparatus. That is, the CAD apparatus holds, for example, each diagnosis-assisting algorithm corresponding to a target tissue region, such as a lung field region or a liver region. The CAD apparatus executes a diagnosis-assisting algorithm corresponding to a target tissue region extracted from a CT image for diagnosis processing.

The CT image has a wide region. It is technically difficult to specify the position of a liver from the CT image. Even if it is possible to specify the position of a liver from the CT image, long processing time is taken until the position of the liver is specified. Therefore, when the position of a liver is specified from the CT image, often, a user sets, for example, a reference position, or designates a region having the possibility that a liver exists.

As such, the operating of designating the extracted position of a target tissue region to be extracted from a CT image is performed by a user. Therefore, execution of the diagnosis-assisting algorithm in the CAD apparatus is made after the operation of designation of the extracted position of a target tissue region by a user. In the CAD apparatus, several minutes are generally required to complete processing of the diagnosis-assisting algorithm.

However, after acquisition of a CT image of a subject by the X-ray CT apparatus, the operation of designating the extracted position of a target tissue region is performed by a user. Thereafter, the processing of the diagnosis-assisting algorithm in the CAD apparatus is performed. Therefore, after the acquisition of a CT image of a subject by the X-ray CT apparatus, the processing of the diagnosis-assisting algorithm is completed, and stand-by time is required to start image reading.

BRIEF SUMMARY OF THE INVENTION

The object of the invention is to provide a medical image diagnosis apparatus, an X-ray CT apparatus, and an image processor that can shorten the stand-by time taken to complete a diagnosis-assisting algorithm, after acquisition of a CT image of a subject.

A medical image diagnosis apparatus according to a first aspect of the invention includes: a designating unit that designates an imaging range of a subject from a projection image for designation of the imaging range; a specifying unit that specifies a specific spot on the projection image; a scanning control unit that performs scanning for generating a three-dimensional medical image of the subject on the basis of the imaging range designated by the designating unit; a region determining unit that finds out a three-dimensional target region from the three-dimensional medical image obtained by the scanning on the basis of the specific spot specified on the projection image; and a detection unit that detects a candidate for an abnormal part in the three-dimensional target region.

An X-ray CT apparatus according to a second aspect of the invention includes: a scanning unit that acquires a projection image for designation of an imaging range of a subject, and designates the imaging range on the projection image to perform scanning of the subject; a reconstruction unit that reconstructs projection data obtained by the scanning to generate a CT image; a specifying unit that specifies a specific spot the projection image for determining a target region where a candidate for an abnormal part is detected on; and a transmission unit that transmits the information of the position of the specific spot.

An image processor according to a third aspect of the invention includes: a receiving unit that receives the information of a specific spot specified on a projection image of a subject, a three-dimensional medical image of the subject, and the projection image; a display unit that displays a sectional image of at least the three-dimensional medical image received by the receiving unit; a region determining unit that finds out a three-dimensional target region from the three-dimensional medical image on the basis of the information of the specific spot on the projection image received by the receiving unit; and a detection unit that detects a candidate for an abnormal part in the three-dimensional target image.

DETAILED DESCRIPTION OF THE INVENTION

Hereinafter, a first embodiment of the invention will be described with reference to the drawings.

Figure 1:
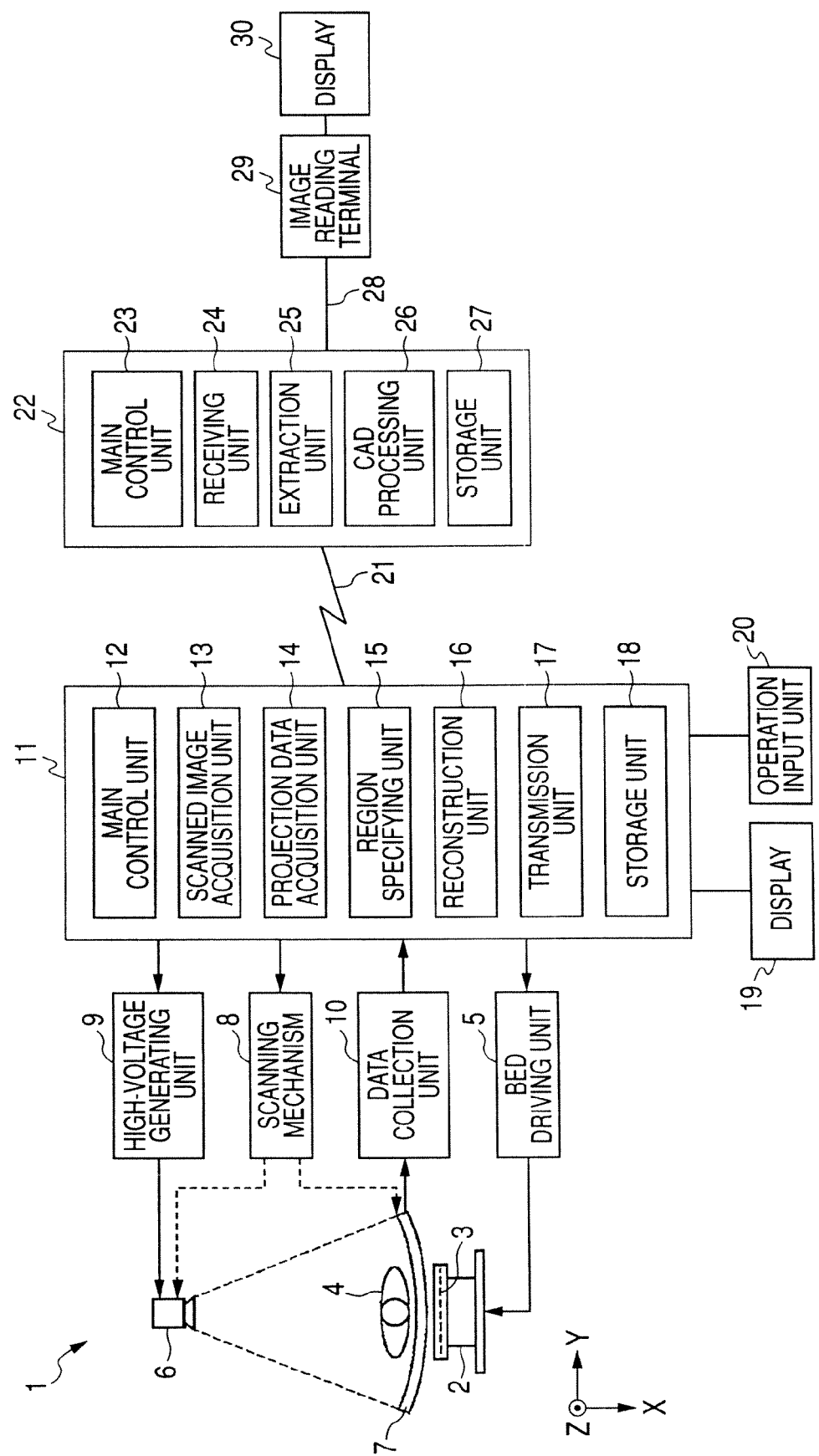
FIG. 1 is an overall constructional view showing a first embodiment of a computer-aided diagnosis (CAD) apparatus according to the invention.

FIG. 1 shows the overall construction of a computer-aided diagnosis (CAD) apparatus. An X-ray CT apparatus 1 includes a bed 2. A ceiling plate 3 is provided in an upper part of the bed 2 so as to be movable in the Z-direction. A subject 4, such as a patient, is placed on the ceiling plate 3. The bed 2 is provided with a bed driving unit 5. The bed driving unit 5 moves the ceiling plate 3 in the Z-direction when a scanned image is acquired, or when CT scanning, such as helical scanning, is performed to acquire a CT image.

An X-ray source 6 and an X-ray detector 7 are provided so as to face each other. The X-ray source 6 and the X-ray detector 7 are provided in a scanning mechanism 8. The scanning mechanism 8 performs, for example, helical scanning, that is, continuously rotates the X-ray source 6 and the X-ray detector 7 together. Along with this, the scanning mechanism 8 delivers a movement control signal to the bed driving unit 5 to move the ceiling plate 3 of the bed 2 in the Z-direction. Thereby, the locus of the movement of the X-ray source 6 is drawn spirally with respect to the subject 4.

A high-voltage generating unit 9 is connected to the X-ray source 6. The high-voltage generating unit 9 supplies a high voltage to the X-ray source 6 to make X-rays emitted from the X-ray source 6. The X-rays are radiated to the subject 4, are transmitted through subject 4, and enter the X-ray detector 7.

The X-ray detector 7 is formed, for example, by arraying a plurality of light-receiving elements. The X-ray detector 7 receives the X-rays transmitted through the subject 4, and outputs an X-ray detection signal according to the quantity of the received X-rays to every light-receiving element. A data collection unit 10 is connected to the X-ray detector 7.

The data collection unit 10 converts each X-ray detection signal of every light-receiving element output from the X-ray detector 7 into a voltage signal, amplifies the converted signal, and converts the amplified signal into a digital signal.

An X-ray CT control unit 11 is made up of a computer. The X-ray CT control unit 11 executes a control program, which is stored in advance, to thereby deliver a starting command of scanning operation to the scanning mechanism 8. Along with this, the X-ray CT control unit 11 delivers a movement command to the bed driving unit 5, delivers a high-voltage supply command to the high-voltage generating unit 9, and performs control of acquisition operation of a scanned image of the subject 4, or control of acquisition operation of plural kinds of projection data of the subject 4.

The X-ray CT control unit 11, as shown in the functional block diagram in FIG. 1, includes a main control unit 12 having a CPU, a scanned image acquisition unit 13, a projection data acquisition unit 14, a region designating unit 15, a reconstruction unit 16, and a transmission unit 17. The X-ray CT control unit 11 includes a storage unit 18. A display 19 and an operation input unit 20 are connected to the X-ray CT control unit 11. The operation input unit 20, which is a user interface, is made up of, for example, an operation panel, etc.

An image server 22 as an image processor is connected to the X-ray CT control unit 11 via a network 21. In addition, although FIG. 1 shows that one X-ray CT apparatus 1 is connected to the image server 22 via the network 21, a plurality of X-ray CT apparatuses 1 are connected to the image server 22 via the network 21 in actuality.

Figure 3:
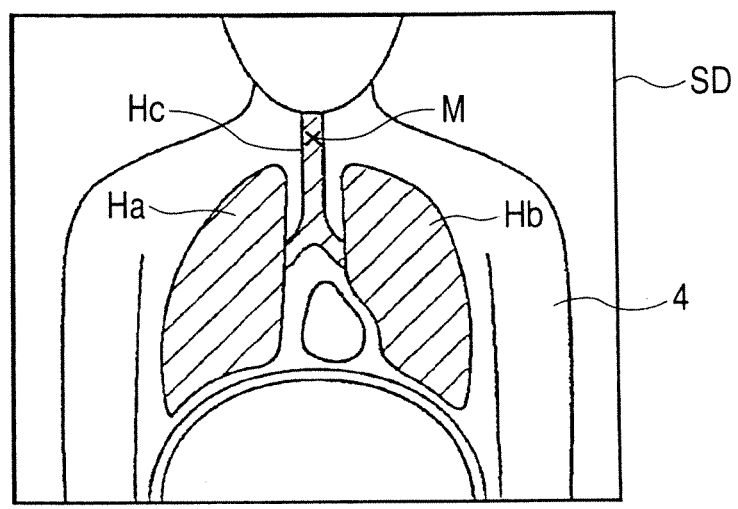
FIG. 3 is a schematic view showing an example of a scanned image of a subject in the apparatus.

The scanned image acquisition unit 13 acquires a two-dimensional scanned image SD of the subject 4 as shown in, for example, FIG. 3 before a CT image of the subject 4 is acquired. The scanned image SD is acquired in order to determine the starting position of CT scanning and the imaging conditions when the CT image is acquired.

Figure 2:
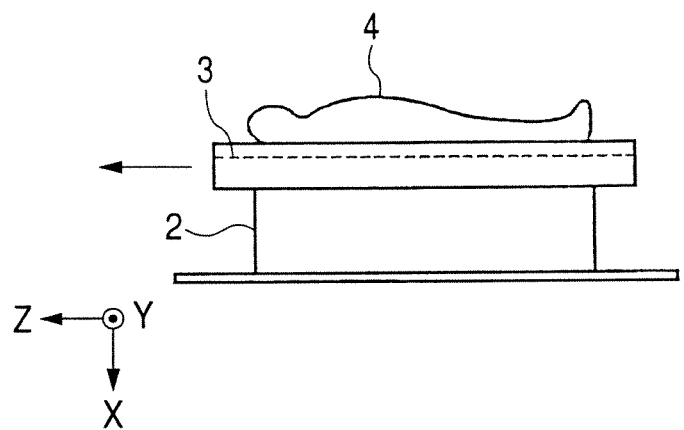
FIG. 2 is a view showing movement of a bed in the apparatus.

The acquisition of the scanned image SD of the subject 4 is as follows. The position of the X-ray source 6 is fixed to a predetermined angle of rotation. The ceiling plate 3 of the bed 2 is moved in the Z direction as shown in FIG. 2. At this time, the X-ray source 6 radiates X-rays to the subject 4. The X-ray detector 7 receives the X-rays transmitted through the subject 4, and outputs an X-ray detection signal according the quantity of the received X-rays to every light-receiving element.

The data collection unit 10 converts each X-ray detection signal of every light-receiving element output from the X-ray detector 7 into a voltage signal, amplifies the converted signal, and converts the amplified signal into a digital signal.

The scanned image acquisition unit 13 inputs each digital X-ray detection signal from the data collection unit 10, and acquires a two-dimensional scanned image SD of the subject 4 as shown, for example, in FIG. 3 from each digital X-ray detection signal. For example, right and left lungs Ha and Hb, and a bronchus Hc are found in the scanned image SD.

The projection data acquisition unit 14 acquires the projection data according to the quantity of the X-rays transmitted through the subject 4 when CT scanning is performed according to the starting position of the CT scanning and the imaging conditions of a CT image.

The acquisition of the projection data is as follows. First, helical scanning is performed. That is, the X-ray source 6 and the X-ray detector 7 are continuously rotated together, and the ceiling plate 3 of the bed 2 is moved in the Z-direction. At this time, the X-ray source 6 radiates X-rays to the subject 4.

The X-ray detector 7 receives the X-rays transmitted through the subject 4, and outputs an X-ray detection signal according the quantity of the received X-rays to every light-receiving element. The data collection unit 10 converts each X-ray detection signal of every light-receiving element output from the X-ray detector 7 into a voltage signal, amplifies the converted signal, and converts the amplified signal into a digital signal.

The projection data acquisition unit 14 inputs each digital X-ray detection signal from the data collection unit 10, and acquires the projection data of the subject 4 from each digital X-ray detection signal.

The region designating unit 15 displays the scanned image SD shown in, for example, FIG. 3 on the display 19. The region designating unit 15 designates a specific spot M on the scanned image SD, for example, by a two-dimensional (2D) seed point "•", according to a user's operation instruction from the operation input unit 20 on the display 19.

In FIG. 3, the specific spot M is shown by "X" in order to be shown clearly. The point "•" of the specific spot M on the scanned image SD has two-dimensional positional information on the scanned image SD. The indication of the 2D seed point "•" of the specific spot M on the scanned image SD is performed when the imaging conditions when CT scanning is made from the scanned image SD to acquire and reconstruct each piece of the projection data are determined.

If a target tissue region in the subject 4 is a lung field region, the designated position of the 2D seed point "•" of the specific spot M on the scanned image SD is designated onto the bronchus Hc of the subject 4 on the scanned image SD as shown in, for example, FIG. 3. Air exists in the right and left lungs Ha and Hb and the bronchus Hc. A CT value over the air in a CT image shows, for example, −500 or less.

Accordingly, if the 2D seed point "•" of the specific spot M is designated onto the bronchus of the subject 4, the right and left lungs Ha and Hb of the subject 4 can be extracted by connecting CT values of −500 or less in the CT image.

Figure 4:
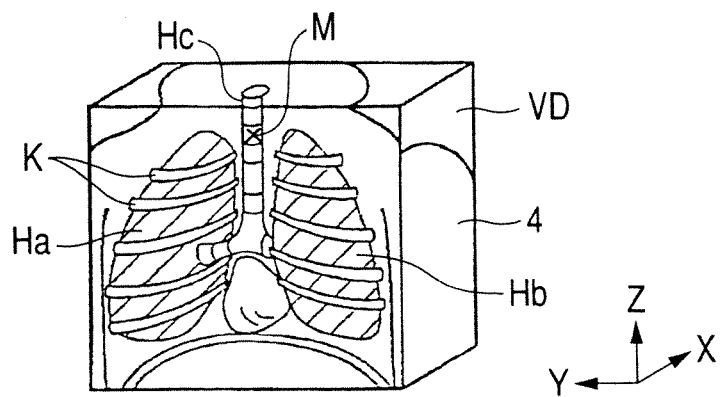
FIG. 4 is a schematic view showing an example of a three-dimensional CT image acquired by reconstructing projection data in the apparatus.

The reconstruction unit 16 receives plural kinds of projection data of the subject 4 from the projection data acquisition unit 14, and reconstructs each piece of the projection data to acquire a three-dimensional CT image VD as shown in, for example, FIG. 4. The CT image VD also includes the right and left lungs Ha and Hb, bronchus Hc, ribs K, etc. of the subject 4.

The transmission unit 17 transmits to the image server 22 via the network 21 the two-dimensional scanned image SD of the subject 4 acquired by the scanned image acquisition unit 13, the projection data of the subject 4 acquired by the projection data acquisition unit 14, the positional information of the 2D seed point "•" of the specific spot M on the scanned image SD acquired by the region designating unit 15, and the three-dimensional CT image VD acquired by the reconstruction unit 16.

The storage unit 18 temporarily stores the two-dimensional scanned image SD of the subject 4 acquired by, for example, the scanned image acquisition unit 13, the projection data of the subject 4 acquired by the projection data acquisition unit 14, and the positional information of the 2D seed point "•" of the specific spot M on the scanned image SD acquired by the region designating unit 15.

The image server 22 receives the scanned image SD and plural kinds of projection data on the subject 4 transmitted from the X-ray CT apparatus 1, and reconstructs each piece of the projection data to acquire a CT image. The image server 22 includes a main control unit 23 having a CPU, a receiving unit 24, an extraction unit 25, and a CAD processing unit 26 as shown in a functional block of FIG. 1.

The image server 22 is provided with a storage unit 27. An image reading terminal 29 is connected to the image server 22 via a network 28. In addition, although FIG. 1 shows that one image reading terminal 29 is connected to the image server 29 via the network 28, a plurality of image reading terminal 29 are connected to the image server 29 via the network 28 in actuality.

The receiving unit 24 receives via the network 21 the two-dimensional scanned image SD of the subject 4 transmitted from the transmission unit 17 of the X-ray CT apparatus 1, plural kinds of projection data of the subject 4, and the positional information of the 2D seed point "•" of the specific spot M on the scanned image SD.

Figure 5:
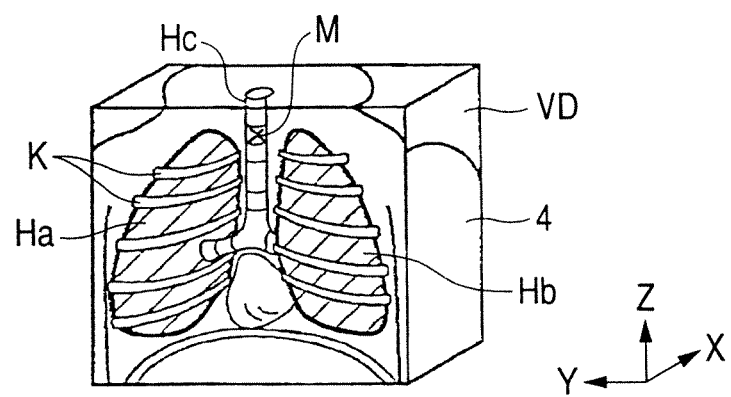
FIG. 5 is a schematic view showing right and left lungs extracted from the CT image in the apparatus.

The extraction unit 25 extracts three-dimensional target regions, for example, right and left lungs Ha and Hb in the subject 4 in the CT image VD as shown in, for example, FIG. 5, on the basis of the 2D seed point "•" of the specific spot M on the scanned image SD shown in, for example, FIG. 3. In addition, for example, the right and left lungs Ha and Hb of the subject 4, which have been extracted, are shown by a thick line in FIG. 5 so as to be shown clearly.

Figure 6:
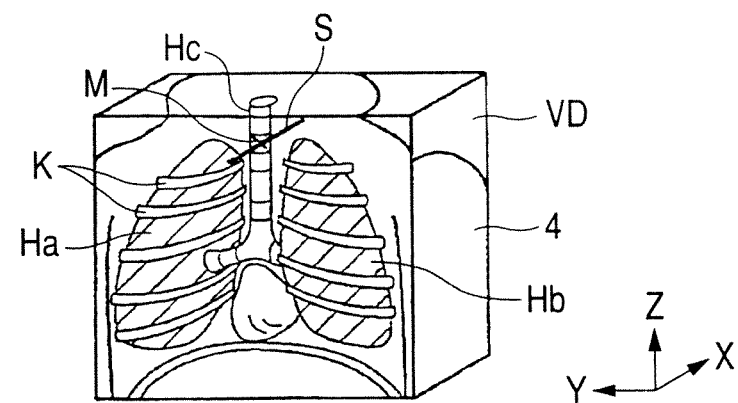
FIG. 6 is a schematic view showing a straight line acquired by projecting a point into the CT image in the apparatus.

Specifically, if the target tissue region is, for example, the right and left lungs Ha and Hb of the subject 4, the extraction unit 25 first projects the 2D seed point "•" of the specific spot M on the scanned image SD designated by the region designating unit 15, to thereby acquire a segment S as shown in, for example, FIG. 6. The segment S extends, for example, from the front surface of the subject 4 towards the rear surface thereof, that is, in the X direction, and passes through the bronchus Hc. During imaging of the scanned image SD and during imaging of the CT image VD, the position of the subject 4 does not change on the bed 2. Accordingly, there is a correspondence relationship in coordinate values between the scanned image SD and the CT image VD.

Figure 7:
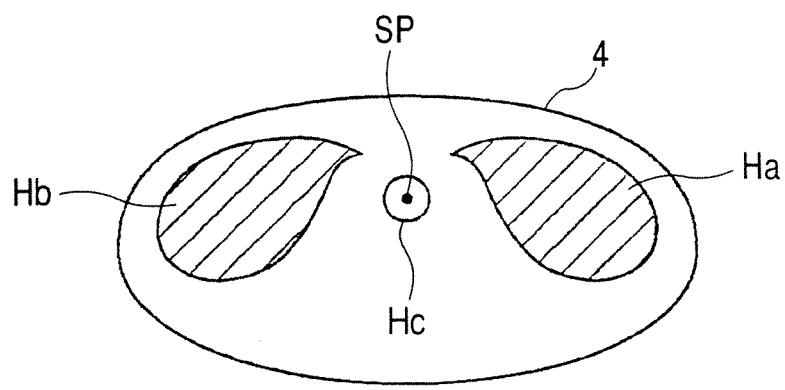
FIG. 7 is a view showing a seed point set on a central axis of a bronchus in the CT image in the apparatus.

Next, the extraction unit 25 searches the bronchus Hc on the basis of each CT value on the segment S, and sets a midpoint of the bronchus Hc, that is, sets three-dimensional (3D) seed point SP on the central axis of the cylindrical bronchus Hc as shown in FIG. 7. The 3D seed point SP has three-dimensional information. Air exists in the bronchus Hc. A CT value within the bronchus Hc in the CT image VD shows, for example, −500 or less.

Accordingly, as for the search of the bronchus Hc, the region of the bronchus Hc is found out by the extraction unit 25 by connecting individual CT values of −500 or less in the CT image VD, and the midpoint of the bronchus Hc is searched from this region. At this time, since the air region outside the subject 4, that is, outside a patient's body should include an end point of a straight line, the region of the bronchus Hc can be specified if a region not including the end point is searched.

Next, the extraction unit 25 searches and connects certain CT values using the 3D seed point SP, that is, the same CT values as the 3D seed point SP having a CT value of −500 or less, from the CT image VD. The extraction unit 25 determines the regions of the connected CT values as the right and left lungs Ha and Hb and bronchus Hc of the subject 4. In this case, the extraction unit 25 finds out as the right and left lungs Ha and Hb of the subject 4 the regions the CT values of which are −500 or less and are connected to the 3D seed point SP, using the 3D seed point SP set in the bronchus Hc, for example, by a region expansion method.

The CAD processing unit 26 detects a candidate for an abnormal part from, for example, the right and left lungs Ha and Hb of the subject 4 that is a three-dimensional target region. That is, the CAD processing unit 26 stores each diagnosis-assisting algorithm for a lung or liver. The CAD processing unit 26 executes a diagnosis-assisting algorithm corresponding to a target tissue region extracted by, for example, the extraction unit 25, for example, the right and left lungs Ha and Hb of the subject 4. Thereby, the CAD processing unit 26 detects disease information from the right and left lungs Ha and Hb of the subject 4, for example, the feature or part of a disease, such as a lung cancer, of the right and left lungs Ha and Hb, and finds out the feature of the disease numerically.

The image reading terminal 29 includes a display 30. The image reading terminal 29 gets an access to the image server 22 via the network 28, detects the feature or part of a disease, such as a lung cancer, in the CT image VD or right and left lungs Ha and Hb of the subject 4, and receives the data obtained by digitalizing the feature of the disease to display the data on the display 30.

Next, the operation of the diagnosis assistance by the apparatus constructed as described above will be described.

The subject 4, such as a patient, is placed on the bed 2. Before a CT image is acquired, a scanned image SD of the subject 4 is acquired. The scanning mechanism 8 fixes the position of the X-ray source 6 to a predetermined angle of rotation. The bed driving unit 5 moves the ceiling plate 3 of the bed 2 in the Z direction as shown in FIG. 2. At this time the high-voltage generating unit 9 supplies the X-ray source 6 with a high voltage.

The X-ray source 6 radiates X-rays onto the subject 4. The X-rays are transmitted through the subject 4 and enter to the X-ray detector 7. The X-ray detector 7 receives the X-rays transmitted through the subject 4, and outputs an X-ray detection signal according the quantity of the received X-rays to every light-receiving element. The data collection unit 10 converts each X-ray detection signal of every light-receiving element output from the X-ray detector 7 into a voltage signal, amplifies the converted signal, and converts the amplified signal into a digital signal. The scanned image acquisition unit 13 inputs each digital X-ray detection signal from the data collection unit 10, and acquires a two-dimensional scanned image SD of the subject 4 as shown, for example, in FIG. 3 from each digital X-ray detection signal.

Next, the region designating unit 15 displays the scanned image SD shown in, for example, FIG. 3 onto the display 19. A user observes the scanned image SD displayed on the display 19, and operates the operation input unit 20 to designate a specific spot M on the scanned image SD by a 2D seed point "•". If the target tissue region in the subject 4 is a lung field region, the position of the 2D seed point "•" is designated onto the bronchus Hc of the subject 4 on the scanned image SD as shown in, for example, FIG. 3.

In addition, the main control unit 12 determines the imaging conditions when CT scanning is made from the scanned image SD to acquire and reconstruct each piece of the projection data, for example, the values of a high voltage, a current, etc. to be applied to the X-ray source 6.

Next, imaging of a CT image VD of the subject 4 is performed. At this time, the subject 4 does not move on the bed 2 during imaging of the scanned image SD, and during imaging of the CT image VD. The scanning mechanism 8 performs, for example, helical scanning. That is, the X-ray source 6 and the X-ray detector 7 are continuously rotated together. Along with this, the bed driving unit 5 moves the ceiling plate 3 of the bed 2 in the Z-direction. Thereby, the locus of the movement of the X-ray source 6 is drawn spirally with respect to the subject 4.

During the helical scanning, the X-ray source 6 radiates X-rays having a quantity of X-rays according to imaging conditions onto the subject 4. The X-rays are transmitted through the subject 4 and enter to the X-ray detector 7. The X-ray detector 7 receives the X-rays transmitted through the subject 4, and outputs an X-ray detection signal according to the quantity of the received X-rays to every light-receiving element.

The data collection unit 10 converts each X-ray detection signal of every light-receiving element output from the X-ray detector 7 into a voltage signal, amplifies the converted signal, and converts the amplified signal into a digital signal.

The projection data acquisition unit 14 inputs each digital X-ray detection signal from the data collection unit 10, and acquires the projection data of the subject 4 from each digital X-ray detection signal.

The reconstruction unit 16 receives plural kinds of projection data of the subject 4 from the projection data acquisition unit 14, and reconstructs each piece of the projection data to acquire a three-dimensional CT image VD as shown in, for example, FIG. 4. The CT image VD also includes the right and left lungs Ha and Hb, bronchus Hc, ribs K, etc. of the subject 4.

Next, the transmission unit 17 transmits to the image server 22 via the network 21 the two-dimensional scanned image SD of the subject 4 acquired by the scanned image acquisition unit 13, the positional information of the 2D seed point "•" of the specific spot M on the scanned image SD acquired by the region designating unit 15, and the three-dimensional CT image VD acquired by the reconstruction unit 16.

On the other hand, the receiving unit 24 of the image server 22 receives via the network 21 the two-dimensional scanned image SD of the subject 4 transmitted from the transmission unit 17 of the X-ray CT apparatus 1, the positional information of the 2D seed point "•" of the specific spot M on the scanned image SD, plural kinds of projection data of the subject 4, and the three-dimensional CT image VD.

Next, the extraction unit 25 extracts the right and left lungs Ha and Hb in the subject 4 in the CT image VD as shown in, for example, FIG. 5, on the basis of the 2D seed point "•" of the specific spot M on the scanned image SD shown in, for example, FIG. 3. The extraction processing of the right and left lungs Ha and Hb from the CT image VD can be executed immediately after the three-dimensional CT image VD has been received because the 2D seed point "•" is already designated on the scanned image SD.

That is, there is a correspondence relationship in coordinate values between the scanned image SD and the CT image VD. Thereby, if the target tissue region is, for example, the right and left lungs Ha and Hb of the subject 4, the extraction unit 25 projects the 2D seed point "•" of the specific spot M on the scanned image SD onto the CT image VD, to thereby acquire a segment S, for example, extending from the front surface of the subject 4 to the rear surface thereof, as shown in, for example, FIG. 6.

Next, the extraction unit 25 connects individual CT values of −500 or less in the CT image VD to find out the region of the bronchus Hc, and sets the midpoint of the bronchus Hc from this region, that is, sets a three-dimensional seed point SP on the central axis of the cylindrical bronchus Hc as shown in FIG. 7. At this time, since the air region outside the subject 4, that is, outside a patient's body should include an end point of a straight line, the region of the bronchus Hc can be specified if a region not including the end point is searched.

Next, the extraction unit 25 searches and connects certain CT values using the 3D seed point SP, that is, the same CT values as the 3D seed point SP having a CT value of −500 or less, from the CT image VD. The extraction unit 25 determines the regions of the connected CT values as the right and left lungs Ha and Hb and bronchus Hc of the subject 4. In this case, the extraction unit 25 finds out as the right and left lungs Ha and Hb of the subject 4 as shown in FIG. 5 the regions the CT values of which are −500 or less and are connected to the 3D seed point SP, using the 3D seed point SP set in the bronchus Hc, for example, by a region expansion method.

In addition, the regions of the right and left lungs Ha and Hb also include the lungs Ha and Hb and an airway, and also include tiny holes, such as blood vessels, in the right and left lungs Ha and Hb. Each of the holes can be removed by shaping a region using erosion processing, dilation processing, a region expansion method, etc.

Next, the CAD processing unit 26 executes a diagnosis-assisting algorithm corresponding to the right and left lungs Ha and Hb of the subject 4 shown in, for example, FIG. 5, which is extracted by the extraction unit 25. The CAD processing unit 26 detects disease information from the right and left lungs Ha and Hb of the subject 4, for example, the feature or part of a disease, such as a lung cancer, of the right and left lungs Ha and Hb, by execution of the diagnosis-assisting algorithm, and finds out the feature of the disease numerically.

The image reading terminal 29 receives a user's operation instruction, gets an access to the image server 22 via the network 28, detects the feature or part of a disease, such as a lung cancer, in the CT image VD or right and left lungs Ha and Hb of the subject 4, and receives the data obtained by digitalizing the feature of the disease to display the data on the display 30. Thereby, a user such as an image reading doctor sees the feature or part of the disease of a liver cancer, etc., in the CT image VD or livers Ha and Hb of the subject 4 displayed on the display and feature of the disease digitalized, and then performs image reading of the disease such as a liver cancer.

As described above, according to the above first embodiment, a 2D seed point "•" of the specific spot M on the scanned image SD of the subject 4 is designated, the right and left lungs Ha and Hb, for example, in the subject 4 in the CT image VD is extracted on the basis of the 2D seed point "•" on the scanned image SD, a diagnosis-assisting algorithm corresponding to the right and left lungs Ha and Hb is executed to detect the feature or part of a disease, such as a lung cancer, of each of the right and left lungs Ha and Hb, the feature of the disease is found out numerically.

Thereby, it is possible to execute a diagnosis-assisting algorithm that automatically extracts the right and left lungs Ha and Hb continuously from when the CT image VD of the subject 4 is acquired, detects the feature or part of a disease, such as a lung cancer, of each of the right and left lungs Ha and Hb, and finds out the feature of the disease numerically.

As a result, during a period before the start of image reading after imaging by the X-ray CT apparatus 1 in, for example, a hospital, it is possible to automatically perform extraction of the right and left lungs Ha and Hb, and execution of a diagnosis-assisting algorithm for each of the right and left lungs Ha and Hb. However, at a point of time of start of the image reading, the detection result of the feature or part of a disease, such as a lung cancer, of each of the right and left lungs Ha and Hb or the result obtained by digitalizing the feature of the disease is already obtained. Thus, the stand-by time of a user can be shortened. Also, user's waiting time can be eliminated.

Next, a second embodiment of the invention will be described with reference to the drawings. In addition, since the construction of the present apparatus is the same as that of FIG. 1, differences will be described by the aid of FIG. 1. The present apparatus detects the feature or part of a disease, such as a liver cancer, in a liver region as a target tissue region in the subject 4, and finds out the feature of the disease numerically.

Figure 8:
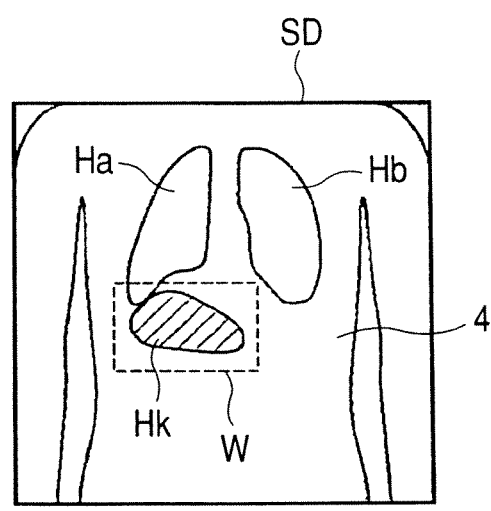
FIG. 8 is a schematic view of a scanned image including a liver acquired according to a second embodiment a computer-aided diagnosis apparatus according to the invention.

The region designating unit 15 displays a scanned image SD shown in, for example, FIG. 8 onto the display 19. A liver Hk is displayed in the scanned image SD. The region designating unit 15 designates, for example, a rectangular frame W as a specific spot M on a scanned image SD by a user's operation instruction from the operation input unit 20 on the display 19. The frame W is designated as a two-dimensional region surrounding the liver Hk.

The extraction unit 25 projects onto a CT image a frame W designated by the region designating unit 15 through a liver region extraction technique that is a well-known technique, for example, a technique not using a seed point, and extracts the liver Hk from within a region within a rectangular parallelepiped obtained by the projection of the frame W.

Figure 9:
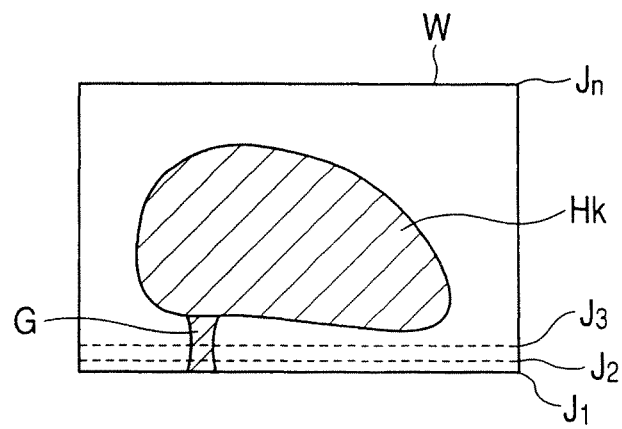
FIG. 9 is a schematic view showing the operation of extraction of the liver by the apparatus.
Figure 10:
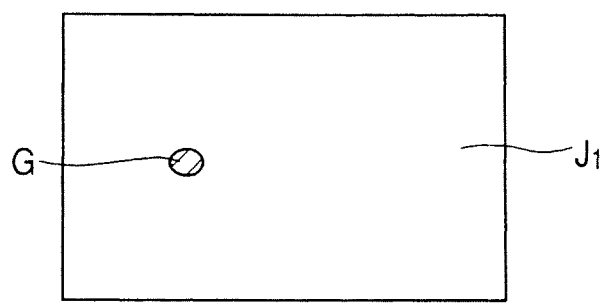
FIG. 10 is a schematic view showing a plane image adjacent to a portal.

In addition, the extraction unit 25 projects onto a CT image a frame W designated by the region designating unit 15 as shown, for example, FIG. 8, through a technique using a seed point that is a well-known technique. A portal G that carries the blood collected from abdominal viscera, such as the stomach, to the liver Hk, exists in the liver Hk. The extraction unit 25, as shown in FIG. 9, detects a plane image $J_1$ touching the rectangular parallelepiped portal G acquired by projecting the frame W onto the CT image. FIG. 10 shows a schematic view of the plane image $J_1$ touching the portal G. The portal G appears on an image surface J. In addition, the liver Hk and the portal G distinctly appear on the CT image by injection of a contrast medium. That is, the liver Hk and the portal G are different in CT value from other parts.

The extraction unit 25 detects the portal G from the plane image $J_1$ and determines a seed point within the portal G.

Next, the extraction unit 25 searches continuous CT values that are CT values within a predetermined range with respect to the CT value of the seed point. In this case, the extraction unit 25 searches continuous CT values that are CT values within a predetermined range with respect to the CT valve of the seed point for every plane image $J_1$ to $J_n$ having every predetermined interval from the plane image $J_1$ touching the portal G.

As a result of the search, the extraction unit 25 extracts a region of the continuous CT values as the liver Hk.

Next, the operation of the diagnosis assistance by the apparatus constructed as described above will be described.

The subject 4, such as a patient, is placed on the bed 2. Similarly to the above, before a CT image is acquired, a scanned image SD of the subject 4 as shown in FIG. 8 is acquired.

Next, the region designating unit 15 displays the scanned image SD shown in, for example, FIG. 8 onto the display 19. A user observes the scanned image SD displayed on the display 19, and operates the operation input unit 20 to designate a rectangular frame W of a two-dimensional region including, for example, a liver Hk as a specific spot M on the scanned image SD.

Next, the subject 4 holds the same posture as that at the time of imaging of the scanned image SD. In this state, similarly to the above, for example, helical scanning is performed. Thereby, imaging of a CT image VD for the subject 4 is performed.

The projection data acquisition unit 14 inputs each digital X-ray detection signal from the data collection unit 10, and acquires the projection data of the subject 4 from each digital X-ray detection signal.

Next, the reconstruction unit 16 receives plural kinds of projection data of the subject 4 from the projection data acquisition unit 14, and reconstructs each piece of the projection data to acquire a three-dimensional CT image VD.

Next, the transmission unit 17 transmits to the image server 22 via the network 21 the two-dimensional scanned image SD of the subject 4 shown in FIG. 8, the positional information of the rectangular frame W designated onto the scanned image SD, the projection data of the subject 4, and the three-dimensional CT image VD acquired by the reconstruction unit 16.

On the other hand, the receiving unit 24 receives via the network 21 the two-dimensional scanned image SD of the subject 4 shown in FIG. 8, the positional information of the rectangular frame W designated onto the scanned image SD, the projection data of the subject 4, and the three-dimensional CT image VD acquired by the reconstruction unit 16.

Next, the extraction unit 25 projects onto a CT image a frame W designated by the region designating unit 15 through a liver region extraction technique that is a well-known technique, for example, a technique not using a seed point, and extracts the liver Hk from within a region within a rectangular parallelepiped obtained by the projection of the frame W.

Further, the extraction unit 25 determines a seed point within a portal that carries the blood collected from abdominal viscera, such as the stomach, to the liver Hk, through a technique using a seed point that is a well-known technique. Next, the extraction unit 25 searches continuous CT values that are CT values within a predetermined range with respect to the CT value of the seed point. Also, the extraction unit 25 extracts a region of the continuous CT values as the liver Hk.

Further, the extraction unit 25 projects onto a CT image a frame W designated by the region designating unit 15 as shown, for example, FIG. 8, through a technique using a seed point that is a well-known technique. The extraction unit 25 searches a plane image $J_1$ touching the rectangular parallelepiped portal G acquired by projecting the frame W onto the CT image as shown in FIG. 9.

The extraction unit 25 searches the portal G from on the plane image $J_1$, and determines a seed point within the portal G.

Next, the extraction unit 25 searches continuous CT values that are CT values within a predetermined range with respect to the CT value of the seed point. In this case, the extraction unit 25 searches continuous CT values that are CT values within a predetermined range with respect to the CT valve of the seed point for every plane image $J_1$ to $J_n$ having every predetermined interval from the plane image $J_1$ touching the portal G.

As a result of the above search, the extraction unit 25 extracts a region of the continuous CT values as the liver Hk.

Next, the CAD processing unit 26 executes a diagnosis-assisting algorithm corresponding to the liver Hk of the subject 4 extracted by the extraction unit 25. Thereby, the CAD processing unit 26 detects disease information from the liver Hk of the subject 4, for example, the feature or part of a disease, such as a liver cancer, of the liver Hk, and finds out the feature of the disease numerically.

The image reading terminal 29 receives a user's operation instruction, gets an access to the image server 22 via the network 28, detects the feature or part of a disease, such as a liver cancer, in the CT image VD or liver Hk of the subject 4, and receives the data obtained by digitalizing the feature of the disease to display the data on the display 30. Thereby, a user, such as an image reading doctor, sees the feature or part of the disease of a liver cancer, etc., in the CT image VD or liver Hk of the subject 4 displayed on the display, and the feature of the disease digitalized, and then performs imaging reading of the disease, such as a liver cancer.

As described above, according to the above second embodiment, a frame W surrounding to the liver Hk on the scanned image SD of the subject 4 is designated, the liver Hk is extracted from the frame W of the scanned image SD, and a diagnosis-assisting algorithm corresponding to the liver Hk is executed. Accordingly, similarly to the first embodiment, during a period before the start of image reading after imaging by the X-ray CT apparatus 1 in, for example, a hospital, it is possible to automatically perform extraction of the liver Hk, and execution of a diagnosis-assisting algorithm for the liver Hk.

Thereby, at a point of time of start of the image reading, the detection result of the feature or part of a disease, such as a liver cancer, of the liver Hk or the result obtained by digitalizing the feature of the disease is already obtained. Accordingly, the stand-by time of a user can be shortened. Also, user's waiting time can be eliminated.

Next, a third embodiment of the invention will be described with reference to the drawings. In addition, since the construction of the present apparatus is the same as that of FIG. 1, differences will be described by the aid of FIG. 1. The present apparatus detects the feature or part of a disease, such as a liver cancer, in a liver region as a target tissue region in the subject 4, and finds out the feature of the disease numerically.

Figure 11:
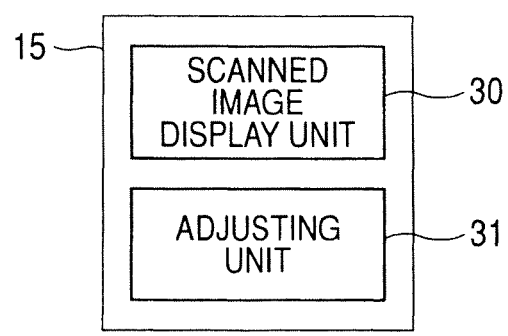
FIG. 11 is a block diagram of a region designating unit in a third embodiment of the computer-aided diagnosis apparatus according to the invention.
Figure 12:
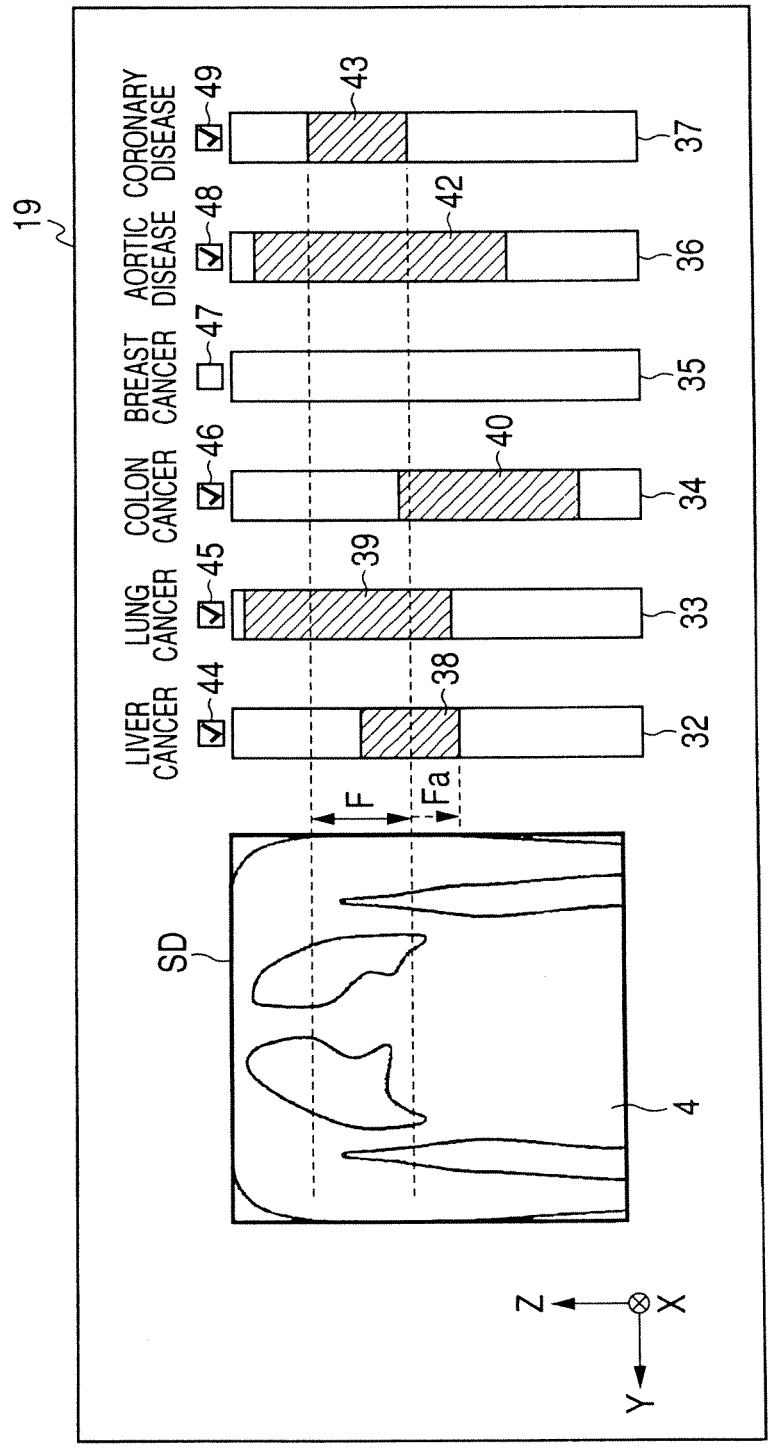
FIG. 12 is a view showing an adjusting row of a target tissue region in a region designate unit in the apparatus.

The region designating unit 15, as shown in FIG. 11, has a scanned image display unit 30, and an adjusting unit 31. The adjusting unit 31 displays the scanned image SD as shown in FIG. 12 onto, for example, the display 19.

The adjusting unit 31 allows adjustment of the range of a region that corresponds in positional relationship to a scanned image SD displayed by the scanned image display unit 30, and that is extracted from a CT image for each of a plurality of target tissue regions, for example, a liver, lungs, a large intestines, breasts, main arteries, and coronary arteries in the subject 4 of a patient.

Specifically, the adjusting unit 31 displays graph display regions 32 to 37 for diagnosing a liver cancer, a lung cancer, a colon cancer, a breast cancer, an aortic disease, and a coronary disease onto, for example, the display 19. The individual graph display regions 32 to 37 are arranged next to the scanned image SD and displayed parallel to one another, on the screen of the display 19. The individual graph display regions 32 to 37 have an equal length in the Z direction of the scanned image SD, i.e., in the height direction of the subject 4.

The individual graph display regions 32 to 37 display individual gray regions 38 to 43, respectively. The individual gray regions 38 to 43 display, for example, gray colors for specifying the target tissue regions including a liver, lungs, a large intestines, breasts, main arteries, and coronary arteries. The individual gray regions 38 to 43 may display any colors other, not limited to the gray colors.

The ranges of the individual gray regions 38 to 43 in the Z-direction can be adjusted according to the sizes of the liver, lungs, large intestines, breasts, main arteries, coronary arteries, etc. of the subject 4. The ranges of the individual gray regions 38 to 43 in the Z-direction can be adjusted, for example, by the operation of the operation input unit 20 by a user. For example, although the coronary artery display region 43 is set to a range F, it can be adjusted to a range Fa. The adjustment of each of the individual gray regions 38 to 43 may be made, for example, by adjusting at least any one or both of the upper end and lower end of each of the gray regions 38 to 43.

The adjusting unit 31 displays individual check boxes 44 to 49 above the individual gray regions 38 to 43, respectively, on the screen of the display 19. The individual check boxes 44 to 49 indicates whether or not CAD diagnosis is executed on, for example, the liver, lungs, large intestines, breasts, main arteries, and coronary arteries in the subject 4.

A check mark is input to each of the check boxes 44 to 49, for example, by the operation of the operation input unit 20 by a user. In FIG. 12, for example, check marks are input to the liver, lungs, large intestines, main arteries, and coronary arteries, and any check mark is not input to the breasts. Accordingly, for example, the CAD diagnosis for liver, lungs, large intestines, main arteries, and coronary arteries is performed. The CAD diagnosis for breasts is not performed. In addition, the reason why a gray region is not displayed in the graph display region 35 for breasts is because the CAD diagnosis for breasts is not performed.

If such a region designating unit 15 is used, a scanned image SD of the subject 4 is acquired before a CT image of the subject 4, such as a patient. The scanned image display unit 30 displays the scanned image SD as shown in FIG. 12 onto, for example, the display 19.

Along with this, the adjusting unit 31, as shown in FIG. 12, displays the individual graph display regions 32 to 37 for diagnosing a liver cancer, a lung cancer, a colon cancer, a breast cancer, an aortic disease, and a coronary disease onto, for example, the display 19. The adjusting unit 31 displays the individual check boxes 44 to 49 above the individual gray regions 38 to 43, respectively, on the screen of the display 19.

A check mark is input to each of the check boxes 44 to 49, for example, by the operation of the operation input unit 20 by a user. In FIG. 12, for example, check marks are input to the liver, lungs, large intestines, main arteries, and coronary arteries, and any check mark is not input to the breasts.

On the other hand, the ranges of the gray regions 38 to 43 in the Z-direction can be adjusted, for example, by the operation of the operation input unit 20 by a user. The adjustment of the range of each of the gray regions 38 to 43 in the Z direction is made, for example, by moving at least any one or both of the upper end and lower end of each of the gray regions 38 to 43.

After the imaging by the X-ray CT apparatus 1, the transmission unit 17 transmits to the image server 22 via the network 21 the two-dimensional scanned image SD of the subject 4 shown in, for example, FIG. 12, the Z-direction range information in the gray regions 38 to 43 acquired by the region designating unit 15, the check information in the individual the check boxes 44 to 49, the projection data of the subject 4 acquired by the projection data acquisition unit 14, and the three-dimensional CT image VD acquired by the reconstruction unit 16.

The extraction unit 25 of the image server 22 extracts, for example, a liver region, a lung region, a large intestine region, a main artery region, and a coronary artery region from a CT image on the basis of the Z-direction range information of the gray regions 38 to 43 acquired by the region designating unit 15.

The CAD processing unit 26 selects each diagnosis-assisting algorithm for livers, lungs, large intestines, main arteries, and coronary arteries, according to the check information in the individual check boxes 44 to 49.

The CAD processing unit 26 executes a diagnosis-assisting algorithm for a liver on the liver region extracted from the CT image to detect the feature or part of a disease, such as a liver cancer, in the liver of the subject 4, and finds out the feature of the disease numerically.

Further, the CAD processing unit 26 executes a diagnosis-assisting algorithm for lungs on the lung region extracted from the CT image to detect the feature or part of a disease, such as a lung cancer, in the lungs of the subject 4, and finds outs the feature of the disease numerically.

Similarly to the above, the CAD processing unit 26 executes individual diagnosis-assisting algorithms for large intestines, main arteries, and coronary arteries on the large intestine region, main artery region, and coronary artery region acquired by the CT image to thereby detect the features or parts of individual diseases in the large intestines, main arteries, and coronary arteries, and finds outs the features of these diseases numerically.

As described above, according to the above third embodiment, the individual graph display regions 32 to 37 that allow the adjustment of the range of a region to be extracted from a CT image for each of the livers, lungs, large intestines, breasts, main arteries, and coronary arteries in the subject 4, such as a patient, and the individual check boxes 44 to 49 that indicates whether or not the CAD diagnosis for, for example, livers, lungs, large intestines, breasts, main arteries, and coronary arteries in the subject 4 are displayed in juxtaposition with the scanned image SD.

Thereby, in addition to the effects of the above first embodiments, a region to be extracted from a CT image can be adjusted in accordance with internal organs, such as livers, lungs, large intestines, breasts, main arteries, and coronary arteries. Along with this, a diagnosis-assisting algorithm to be executed in the CAD processing unit 26 can be indicated.

In addition, the invention is not limited to the above embodiments as it is, but the invention can be modified as follows.

For example, the region designating unit 15, the reconstruction unit 16, and the extraction unit 25 can be provided in any one or both of the X-ray CT control unit 11 and the image server 22.

A target tissue region, such as livers, lungs, large intestines, breasts, main arteries, and coronary arteries, from a CT image, may be extracted using a well-known region extraction technique.

Although the image server 22 is used as the image processor, the invention is not limited thereto, and a CAD apparatus body may be used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image diagnosis apparatus comprising:
a designating unit that designates an imaging range of a subject from a two-dimensional projection image for designation of the imaging range;
a specifying unit that specifies a specific seed spot on the two-dimensional projection image;
a scanning control unit that performs scanning for generating a three-dimensional medical image of the subject on the basis of the imaging range designated by the designating unit after the specific seed spot has been specified on the projection image;
a region determining unit that projects the seed spot onto the three-dimensional medical image to determine a three-dimensional target region from the three-dimensional medical image obtained by the scanning on the basis of the specific seed spot specified on the projection image; and
a detection unit that detects a candidate for an abnormal part in the three-dimensional target region.

2. The medical image diagnosis apparatus according to claim 1,
wherein the region determining unit acquires a segment corresponding to the specific seed spot specified on the projection image within the three-dimensional medical image, finds out one point within the three-dimensional target region on the basis of a pixel value on the segment, and extracts the three-dimensional target region from the three-dimensional medical image on the basis of the pixel value of the three-dimensional medical image, using the one point as a starting point.

3. The medical image diagnosis apparatus according to claim 1,
wherein the specifying unit specifies a predetermined range as the specific seed spot within the projection image for designation of the imaging range, and
the region determining unit extracts an image of the three-dimensional target region from the three-dimensional medical image on the basis of a pixel value within the three-dimensional medical image corresponding to the predetermined range specified by the specifying unit.

4. A medical image diagnosis apparatus comprising:
an X-ray CT apparatus; and
an image processing apparatus;
the X-ray CT apparatus including:
a scanning unit that acquires a two dimensional projection image for designation of an imaging range of a subject, and designates the imaging range on the projection image to perform scanning of the subject, thereby obtaining projection data;
a specifying unit that specifies a specific seed spot for determining a target region where a candidate for an abnormal part is detected on the two-dimensional projection image before the scanning is performed by the scanning unit;
a reconstruction unit that reconstructs the projection data to generate a three-dimensional medical image; and
a transmission unit that transmits at least information on the specific seed spot and the three-dimensional medical image; and
the image processing apparatus including:
a receiving unit that receives at least the information on the specific seed spot and the three-dimensional medical image transmitted from the transmission unit;
a display unit that displays a sectional image of at least the three-dimensional medical image received by the receiving unit;
a region determining unit that projects the seed spot onto the three-dimensional medical image to determine a three-dimensional target region from the three-dimensional medical image on the basis of the information on the specific seed spot received by the receiving unit; and
a detection unit that detects a candidate for an abnormal part in the three-dimensional target region.

5. The medical image diagnosis apparatus according to claim 4:
wherein the transmission unit transmits either a CT image or the projection data, together with the information on the specific seed spot on the projection image as the three-dimensional medical image.

6. The medical image diagnosis apparatus according to claim 4,
wherein the region determining unit acquires a segment corresponding to the specific seed spot specified on the projection image within the three-dimensional medical image, finds out one point within the three-dimensional target region on the basis of a pixel value on the segment, and extracts the three-dimensional target region from the three-dimensional medical image on the basis of the pixel value of the three-dimensional medical image, using the one point as a starting point.

7. The medical image diagnosis apparatus according to claim 4,
wherein the specifying unit specifies a predetermined range as the specific seed spot within the projection image for designation of the imaging range, and
the region determining unit extracts an image of the three-dimensional target region from the three-dimensional medical image on the basis of a pixel value within the three-dimensional medical image corresponding to the predetermined range specified by the specifying unit.

8. The medical image diagnosis apparatus according to claim 4, further comprising a display unit that superimposes and displays the abnormal part candidate detected by the detection unit on the three-dimensional reconstructed image.

9. The medical image diagnosis apparatus according to claim 6,
wherein the three-dimensional target region is a lung field region, and
the region determining unit projects a point serving as the specific seed spot specified on the projection image onto the three-dimensional medical image, searches a trachea region on the basis of each pixel value on a segment acquired by the projection, sets the starting point on a middle point of the trachea region on the segment, finds out a region to be connected with the starting point having a predetermined pixel valve, using the starting point, and executes shape processing of the region to be connected to determine the lung field region.

10. The medical image diagnosis apparatus according to claim 7,
wherein the three-dimensional target region is a liver region, and
the region determining unit projects the predetermined range specified by the specifying unit onto the three-dimensional image, and extracts the liver region from the three-dimensional target region obtained by the projection.

11. The medical image diagnosis apparatus according to claim 4,
wherein the display unit displays a sectional image of at least the three-dimensional medical image, and
the region determining unit displays at least one display region on one side of the sectional image of the three-dimensional medical image displayed on the display unit, the display region enabling adjustment of a range in which the three-dimensional target region is extracted from the sectional image of at least the three-dimensional medical image.

12. The medical image diagnosis apparatus according to claim 1, further comprising an input unit for a user to specify the specific seed spot on the projection data.

13. The medical image diagnosis apparatus according to claim 4, further comprising an input unit for a user to specify the specific seed spot on the projection data.

* * * * *